(12) United States Patent
Couillaud et al.

(10) Patent No.: US 10,333,895 B2
(45) Date of Patent: Jun. 25, 2019

(54) ASSIGNING ADDRESSES TO MEDICAL DEVICES IN A RACK

(71) Applicant: Fresenius Vial SAS, Brézins (FR)

(72) Inventors: Frederic Couillaud, Brézins (FR); Lionel Doris, Grenoble (FR)

(73) Assignee: Fresenius Vial SAS, Brezins (FR)

( * ) Notice: Subject to any disclaimer, the term of this patent is extended or adjusted under 35 U.S.C. 154(b) by 693 days.

(21) Appl. No.: 14/761,686

(22) PCT Filed: Jan. 6, 2014

(86) PCT No.: PCT/EP2014/050089
§ 371 (c)(1),
(2) Date: Jul. 17, 2015

(87) PCT Pub. No.: WO2014/111285
PCT Pub. Date: Jul. 24, 2014

(65) Prior Publication Data
US 2015/0351847 A1 Dec. 10, 2015

Related U.S. Application Data

(60) Provisional application No. 61/754,031, filed on Jan. 18, 2013.

(30) Foreign Application Priority Data

Jan. 18, 2013 (EP) .................................... 13305060

(51) Int. Cl.
*G06F 15/16* (2006.01)
*H04L 29/12* (2006.01)
(Continued)

(52) U.S. Cl.
CPC ............ *H04L 61/609* (2013.01); *A61B 50/20* (2016.02); *A61B 50/22* (2016.02); *A61M 5/1413* (2013.01);
(Continued)

(58) Field of Classification Search
CPC .......... A61M 5/1413; A61M 2205/502; A61M 2205/60; A61M 2209/084;
(Continued)

(56) References Cited

U.S. PATENT DOCUMENTS 5,038,317 A * 8/1991 Callan ................... G05B 19/054
700/24
5,065,154 A * 11/1991 Kaiser ................. G06F 12/0676
340/286.07

(Continued)

FOREIGN PATENT DOCUMENTS

| EP | 0 340 325 | 11/1989 |
| EP | 0960627 | 12/1999 |
| WO | 1998/056451 | 12/1998 |

*Primary Examiner* — William G Trost, IV
*Assistant Examiner* — Tan Doan
(74) *Attorney, Agent, or Firm* — Occhiuti & Rohlicek LLP (57) ABSTRACT

A rack for holding at least one medical device, the rack comprises a multiplicity of interfaces for connecting at least one medical device to the rack. Herein, a channel identification device is provided which is constituted to assign an identification code to each of the multiplicity of interfaces and is operable to provide, for a medical device connected with one of the multiplicity of interfaces, the identification code associated with the interface to the medical device or a control device connected to the medical device. In this way, a rack for holding at least one medical device is provided which in an easy manner allows for the identification of the topological position of a medical device on a rack or a system of racks.

12 Claims, 3 Drawing Sheets (51) Int. Cl.
*A61M 5/14* (2006.01)
*G06F 19/00* (2018.01)
*A61B 50/22* (2016.01)
*A61B 50/20* (2016.01)
*G16H 40/63* (2018.01)

(52) U.S. Cl.
CPC ......... *G06F 19/3468* (2013.01); *G16H 40/63* (2018.01); *A61B 2562/226* (2013.01); *A61M 2205/502* (2013.01); *A61M 2205/60* (2013.01); *A61M 2209/084* (2013.01)

(58) Field of Classification Search
CPC .......... A61B 2562/226; A61B 19/0256; A61B 50/20; A61B 50/22; G16H 40/63; G06F 19/3468; G06F 12/0676; G06F 11/006; H04L 61/609; B01L 3/545; B01L 3/5453; G06K 2017/009
USPC ....................................................... 709/245
See application file for complete search history.

(56) References Cited

U.S. PATENT DOCUMENTS

| | | | | |
|---|---|---|---|---|
| 5,613,158 A | * | 3/1997 | Savage | G06F 12/0676 710/9 |
| 5,713,856 A | * | 2/1998 | Eggers | A61M 5/1413 604/65 |
| 5,836,910 A | * | 11/1998 | Duffy | A61M 5/1413 604/65 |

* cited by examiner

FIG 1

ASSIGNING ADDRESSES TO MEDICAL DEVICES IN A RACK

BACKGROUND

The invention relates to a rack for holding at least one medical device according to the preamble of claim 1, to a system comprising multiple racks and to a method for arranging at least one medical device on a rack.

A rack of this kind comprises a multiplicity of interfaces for connecting at least one medical device to the rack.

Racks of this kind serve to fixedly hold and organize medical devices such as infusion pumps to administer fluids, for example medication or nutrients, to a patient in a hospital environment. Such racks in general comprise multiple mechanical interfaces to hold multiple medical devices such that the medical devices via the rack can be organized in a space-efficient manner, for example by forming a vertical stack of medical devices. The rack herein serves as a communication spine providing a communication among the medical devices attached to the rack and between the medical devices and external periphery devices such as a nurse call, a printer, a computer, a barcode reader or an external communication network. Further, the rack serves to supply the medical devices attached to the rack with power.

For example, in a commercially available rack system four medical devices such as medical infusion pumps can be connected to a rack, wherein altogether three racks can be interconnected with each other, hence forming a system of racks capable of carrying at most 3×4=12 medical devices. The racks are interconnected such that the medical devices attached to the racks can communicate with each other and with external periphery devices via communication lines, for example via a communication network such as a local area network (LAN) or the internet.

If the medical devices connected to a system of racks are connected via the racks to a network, typically unique identifiers for logically identifying the medical devices in the network are associated with the medical devices. Such identifiers serve as network addresses and may for example be constituted by the so-called MAC addresses. However, such logical identifiers cannot serve to localize the medical devices on the racks, because from the logical identifiers no conclusions can be drawn with regard to the topological, physical arrangement of the medical devices on the racks.

In common hospital environments, one rack or multiple racks interconnected with each other may be placed at a bedside of a patient and may carry multiple medical devices such as infusion pumps attached to the racks. To control the operation of the medical devices, a control device including a display is used which displays information concerning the medical devices and allows for a controlling of operational parameters, such as the infusion dose or the infusion rate of an infusion pump, by a nurse or another user.

With regard to such control devices and control tools running on such control devices, there is a desire to display the medical devices to be controlled on the display of the control device in the same topological arrangement and order as they are arranged physically on the rack. For this, however, it is necessary to identify the topological position of medical devices on the racks such that their relative position becomes known and can accordingly be displayed on the control device. If a nurse sees the medical devices to be controlled in the same order and arrangement on the control device as the medical devices are physically arranged at the bedside of the patient, the controlling of the devices for the nurse becomes easier, because an association between the displayed devices and the physical devices at the bedside of the patient can intuitively be made. This reduces the risk of control errors.

Further, a control device, by referring to the specific position of a particular medical device on a system of racks, can provide more specific, easier-to-follow instructions for a nurse or can provide more direct instructions or alerts with regard to an alarm condition or an unexpected operational behaviour of a particular medical device. For example, the control device can directly hint at the "second pump from the bottom" or the "third pump from the top" such that the nurse directly and unambiguously gets to know which medical device it is referred to.

There hence is a desire for a rack allowing for topologically identifying the position of a medical device on a rack.

EP 0 960 627 A2 discloses an attachment and carrier unit in the shape of a rack for carrying multiple medical devices in the shape of infusion pumps. Herein, the infusion pumps each are connected to a control device by a separate connection line in a star-shaped wiring, such that the control device can, by interrogating the separate infusion pumps via the separate connection lines, detect the topological position of the infusion pumps on the carrying unit.

Within a system known from WO 98/56451 A1 multiple medical devices such as infusion pumps are connected with each other to form a linear array of modules. WO 98/56451 A1 does not refer to a system including a rack for carrying and mechanically holding multiple medical devices.

SUMMARY

It is an object of the instant invention to provide a rack for holding at least one medical device, a system comprising multiple racks and a method for arranging at least one medical device on a rack which in an easy manner allow for the identification of the topological position of a medical device on a rack or a system of racks.

This object is achieved by a rack according to the features of claim 1.

Accordingly, a rack comprises a channel identification device which is constituted to assign an identification code to each of the multiplicity of interfaces and is operable to provide, for a medical device connected with one of the multiplicity of interfaces, the identification code associated with the interface to the medical device or a control device connected to the medical device.

According to the instant invention, the rack comprises a channel identification device. The channel identification device serves to assign an identification code to each of the interfaces of the rack such that each interface is associated with a unique identification code identifying the interface. The identification code herein is assigned to the interfaces based on the (relative) position of the interfaces on the rack. Hence, by means of the identification code of a particular interface the position of the interface on the rack is identified such that it is possible to determine the relative position of the interface on the rack in relation to other interfaces.

The channel identification device provides the identification code for example to a medical device which is connected to a particular interface, such that the medical device receives knowledge about the identification code of the interface it is connected to. By communicating the identification code to for example an external control device or the like, it then becomes possible to identify to which interface a medical device is connected.

The channel identification device may also directly communicate with the control device, such that the identification code is directly provided from the rack to the control device without the detour via the medical device. For this, the rack comprises appropriate communication circuitry such that a direct communication between the rack and the control device via for example a network can take place.

The number of interfaces of the rack may for example be four, wherein also other numbers of interfaces are possible.

The identification code may for example be constituted by a sequence of bits, wherein the sequence of bits comprises a first portion indicating a sequential position of the interface the identification code is associated with on the rack. The identification code gives, in its first portion, an indication of the relative position of the interface on the rack. By communicating this identification code to the medical device attached to that interface the medical device gets to know to what interface it is connected on the rack. Hence, by communicating the identification code to, for example, an external control device, the control device receives knowledge about the location of the medical device on the rack such that it can display the medical device in its correct position on the rack.

If for example the rack comprises four interfaces, the first portion of the sequence of bits may comprise two bits. The interfaces in this case, in their sequential order, may be associated with the bit words 00, 01, 10, and 11, wherein the bit word 00 may for example correspond to the interface at the lowest position on the rack and the bit word 11 may correspond to the interface at the highest position on the rack.

The sequence of bits may comprise further portions which serve to identify the position of the medical device also in relation to medical devices on other racks connected to the rack the medical device is attached to. For example, a sequence of bits may comprise a second portion indicating whether a second rack is arranged at a first side of a rack, for example below the rack, and/or a third portion indicating whether a third rack is arranged at a second side of the rack, for example above the rack.

The second portion and the third portion of the sequence of bits may for example each correspond to exactly one bit, wherein the bit serves to indicate whether a further rack is arranged at the associated side of the rack. For example, the bit corresponding to the second portion may serve to indicate whether another (second) rack is arranged below the rack in question. The bit corresponding to the third portion may serve to indicate whether another (third) rack is arranged above the rack in question.

Hence, the sequence of bits may take the shape
CBAA,
wherein each capital letter corresponds to one bit. The portion "AA" herein may indicate the sequential position of the interface the identification code is associated with on the rack in question. The portion "C" may serve to indicate whether another rack is arranged below the rack in question. And the portion "B" may serve to indicate whether another rack is placed above the rack in question.

In one embodiment, the general identification means may for example comprise a multiplicity of electronic circuits, for example in the shape of printed circuit boards (PCBs). Herein, an electronic circuit is an operative connection with each of the multiplicity of interfaces such that one electronic circuit is uniquely associated with one interface of the rack. The electronic circuit serves to assign the identification code to the associated interface, wherein in particular the first portion of the sequence of bits representing the identification code, in the above example the portion "AA", may be hard-wired in the electronic circuit associated with the particular interface. This is possible because the location of the interfaces on the rack does not change and hence is static.

The second portion and the third portion of the sequence of bits corresponding to the identification code, however, is not hard-wired in the electronic circuit because such bits change depending on whether further racks are connected to the rack in question. To set the second portion and the third portion of the sequence of bits, the rack may comprise, in one embodiment, a first input port to be connected to a second rack located at a first side of the rack and/or a second input port to be connected to a third rack at a second side of the rack. Herein, the first input port and/or the second input port are connected to the channel identification device, wherein the channel identification device is constituted to detect whether a second and/or a third rack are arranged at the first side and/or the second side of the rack. Hence, the channel identification device, via the first input port and the second input port, detects whether further racks are connected to the rack in question. Based on this detection, the channel identification device then sets the identification code and in particular sets the bits for the second portion and the third portion of the sequence of bits corresponding to the identification code.

If the detection is limited to the detection whether a further rack is present above or below the rack in question, a unique assignment of an identification code to the interfaces of the rack is only possible for a maximum number of three racks interconnected with each other. This is due to the fact that the second portion and the third portion of the sequence of bits would be identical for the middle racks arranged between the two outer most racks, i.e. between the lowest and the highest rack of a vertical stack of racks. To make an identification of the relative position of medical devices attached to the racks possible also for a larger number of racks interconnected with each other, for example the number of racks below and above the rack in question may be detected and communicated. If a rack for example receives the information that two racks are arranged below the rack and three racks are arranged above the rack, it becomes possible to assign a unique identification code to each interface of the rack by combining the first portion of the sequence of bits indicating the relative position of the interface on the rack and the second and third portions of the sequence of bits indicating the numbers of further racks arranged below and above the rack (in this case, the second portion and the third portion of the sequence of bits would contain more than one bit, for example two bits or three bits for indicating the number of further racks below or above the rack in question).

In a particular embodiment, a system comprises multiple racks, wherein at least one medical device may be connected to one of the medical racks and wherein the maximum number of racks of the system is three. In this case, as pointed out above, the identification code can simply be generated by detecting whether a further rack is placed below and/or above the rack in question, such that the electronic circuits for embodying the channel identification device become easy and inexpensive.

A system comprising multiple racks may further more comprise a display device which is in communication connection with the at least one medical device and/or the racks and is constituted to display the topological position of the at least one medical device relative to other medical devices connected to the multiple racks. The medical device for example receives the unique identification code from the rack and communicates the identification code to the display device, which processes the identification code and in this way becomes able to display the topological position of the medical device in relation to the other medical devices on a display. The medical devices, hence, are displayed to a user, for example a nurse in a hospital environment, in the same order as they are physically located for example at the bedside of a patient, such that the association of the displayed devices with the physical devices becomes easy and intuitive.

The object is furthermore achieved by means of a method for arranging at least one medical device on a rack. Herein, a rack comprises a multiplicity of interfaces for attaching at least one medical device to the rack. A channel identification device of the rack assigns an identification code to each of the multiplicity of interfaces and provides, for a medical device connected with one of the multiplicity of interfaces, the identification code associated with the interface to the medical device or a control device connected to the medical device.

The advantages and advantageous embodiments described above for the rack and the system comprising multiple racks apply in an analogous manner also to the method stated above such that it shall be referred to the above description.

Within the method, a medical device advantageously receives the identification code from the channel identification device and transmits the identification code to a display device, or the display device receives the identification code directly from the channel identification device via communication circuitry of the rack. The display device then displays the medical device with its topological position relative to other medical devices connected to the rack such that the order and position of the medical devices on the display equals the order and arrangement of the physical medical devices, for example the infusion pumps, on the bedside of a patient such that an easy and intuitive association may be made between the display and the physical arrangement of the medical devices.

DESCRIPTION OF DRAWINGS

The idea underlying the invention shall subsequently be described in more detail with regard to the embodiments shown in the figures. Herein.

DESCRIPTION

Figure 1:
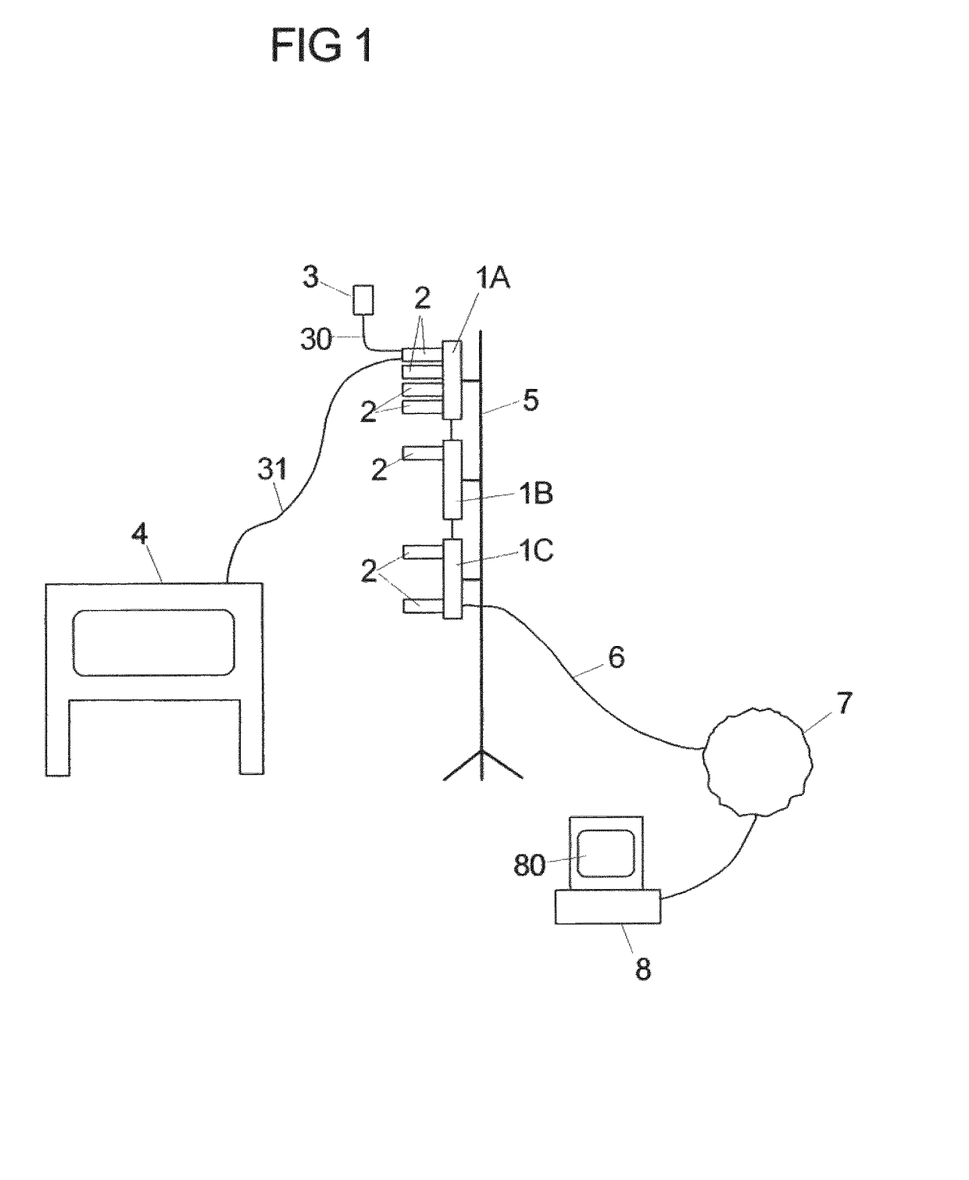
FIG. 1 shows a schematic drawing of a system of racks at the bedside of a patient.

FIG. 1 shows a general arrangement of medical devices 2, as it commonly can be found for example in an intensive care unit in a hospital environment, at the bedside of a patient. Herein, multiple racks 1A, 1B, 1C are arranged on a stand 5 and serve to mechanically hold medical devices 2 in an organized and mechanically fixed fashion. The arrangement of racks 1A, 1B, 1C with the medical devices 2 attached thereto is placed in the vicinity of a patient's bed 4, wherein the medical devices 2 may for example be infusion pumps, such as syringe pumps or volumetric pumps, which serve to administer a fluid such as medication or nutrients contained in a container 3 via infusion lines 30, 31 to a patient.

Typically, such medical devices 2 constituted as infusion pumps are organised on racks 1A, 1B, 1C to form a vertical stack of medical devices 2 on the stand 5. The stand 5 may comprise wheels such that the stand 5 to some extend is movable with respect to the patient's bed 4 or together with the patient's bed 4. The stand 5 may have the shape of a post to which the racks 1A, 1B, 1C for carrying the medical devices 2 are attached and comprises, at its top end, fastening means in the shape of hooks or the like to fasten a number of containers 3 containing medication or nutrients or other fluids to be administered to the patient.

The racks 1A, 1B, 1C serve to arrange the medical devices 2 in an organized fashion at the bedside of a patient. The racks 1A, 1B, 1C herein provide a power supply for the medical devices, ensure a secure and reliable fixation of the medical devices 2, and provide a communication of the medical devices 2 among each other and with an external communication network 7 and with external periphery devices such as a nurse call, a printer, a computer, a monitor or the like.

Conventionally, the medical devices 2 can be fixed to the racks 1A, 1B, 1C and for this are mechanically and electrically connected to the racks 1A, 1B, 1C such that via the racks 1A, 1B, 1C each medical device 2 can be supplied with power and can communicate with other medical devices 2 and with external devices and/or an external communication network 7. The racks 1A, 1B, 1C hence serve as a communication spine providing a communication facility and an electric power supply and embedding the medical devices 2 into a hospital environment including a hospital communication network and a hospital management system.

In the example of FIG. 1, three racks 1A, 1B, 1C are attached to the stand 5. Herein, to each rack 1A, 1B, 1C a multiplicity of medical devices 2 may be attached, for example a maximum of four medical devices 2 per rack 1A, 1B, 1C. If three racks 1A, 1B, 1C are present, hence altogether twelve medical devices 2 can be arranged by means of the racks 1A, 1B, 1C at the bedside of the patient.

At least one of the racks 1A, 1B, 1C—in the given example the lowest rack 1C—is connected via a connection line 6 to a network 7, for example a local area network (LAN), and via the network 7 to a control device 8 including a display device 80. Via the control device 8 the operation of the medical devices 2, for example the pumping operation of infusion pumps, can be controlled and monitored, wherein the control device 8 may be placed at the bedside of the patient or in another, central control room of a hospital.

The control device 8, in one embodiment, may also be attached to the stand 5 or to one of the racks 1A, 1B, 1C. In this case no separate connection line 6 is necessary. The control device 8 rather can be connected directly to one of the racks 1A, 1B, 1C, for example by attaching it to the rack 1A, 1B, 1C at a fixture position provided for attaching a medical device 2 to the rack 1A, 1B, 1C, such that the communication between the medical devices 2 attached to the racks 1A, 1B, 1C and the control device 8 takes place via the racks 1A, 1B, 1C, or attaching it at a fixture position especially provided for attaching the control device 8, or attaching it to fixture position of a rack 1A, 1B, 1C provided for attaching an additional rack.

The control device 8 can for example run a control tool which is referred to as infusion manager for controlling the operation of infusion pumps. Herein, via the infusion manager control parameters such as the infusion rate and the infusion dose for a particular infusion pump can be controlled and monitored such that, via the control device 8, a user, for example a nurse or a physician, may adapt the operation of the infusion pumps constituting the medical devices 2, may monitor the operation and may possibly be alarmed if an error during operation occurs.

On the control device 8 it is desirable to display the medical devices 2 in an arrangement and order which corresponds to the physical arrangement of the medical devices 2 on the racks 1A, 1B, 1C at the bedside of the patient. This is desirable to improve usability of the infusion manager on the control device 8 for a nurse or a physician by allowing for an easy and intuitive input of operational parameters and an easy association of information displayed on or provided by the control device 8 in relation to the medical devices 2.

Commonly, if the racks 1A, 1B, 1C and via the racks 1A, 1B, 1C the medical devices 2 are connected to a network 7, the medical devices 2 are identified in the network 7 logically by their network addresses, for example their MAC addresses. This logical identification, however, does not allow the control device 8 to identify the topological, physical arrangement of the medical devices 2 on the racks 1A, 1B, 1C. In particular, the control device 8 via the network address does not know whether a medical device 2 is placed at the bottom or at the top or somewhere along the vertical stack of medical devices 2 on the racks 1A, 1B, 1C.

Figure 2:
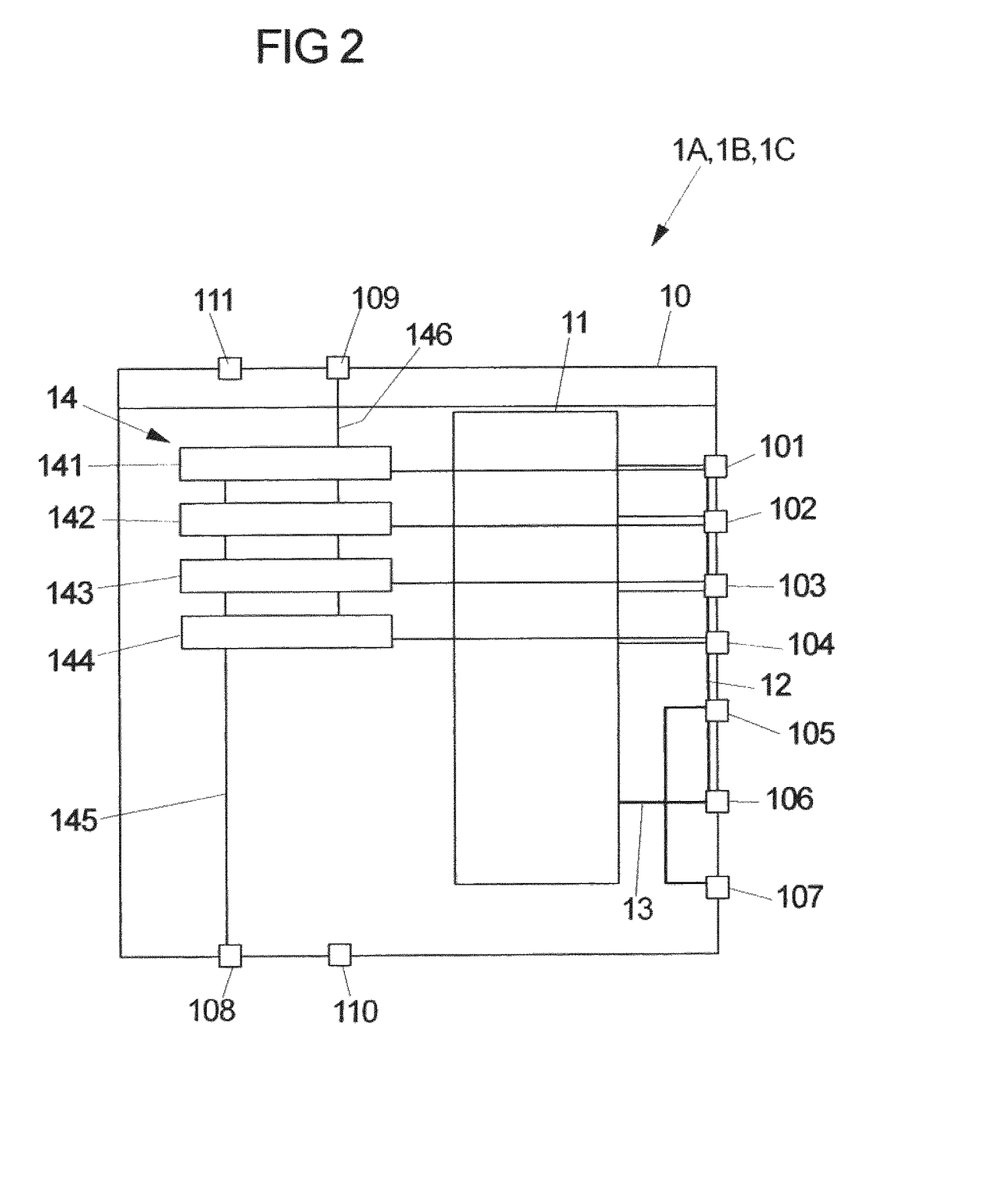
FIG. 2 shows a schematic drawing of the logical structure of a rack.
Figure 3:
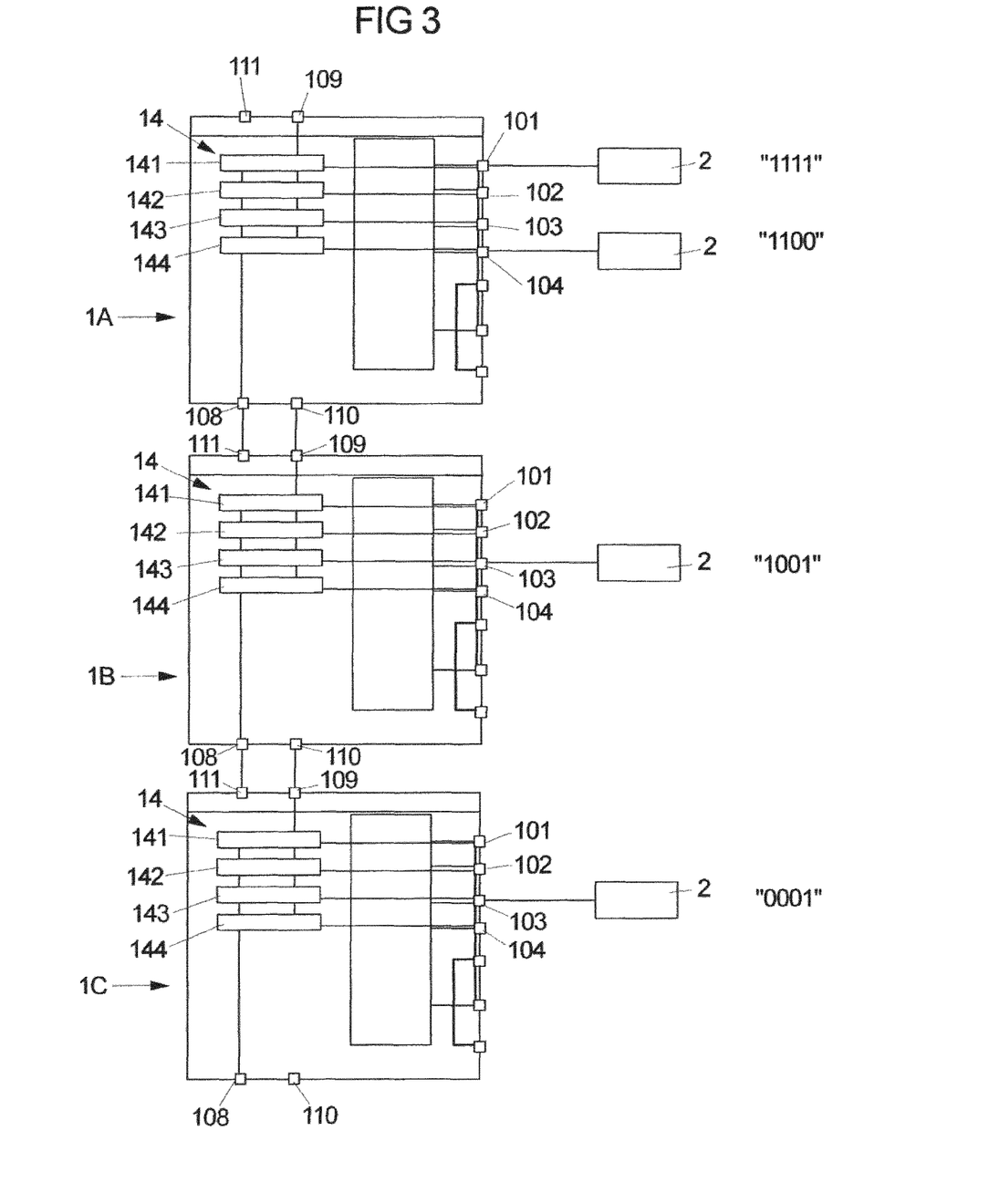
FIG. 3 shows a schematic drawing of the logical structure of three racks interconnected with each other.

To allow the control device 8 to gain knowledge about the topological, physical placement of a medical device 2 on the racks 1A, 1B, 1C in relation to other medical devices 2, the racks 1A, 1B, 1C—as schematically shown in FIGS. 2 and 3—each comprise channel identification device 14 comprising electronic circuits 141-144 in the shape of for example printed circuit boards (PCBs). Herein, each electronic circuit 141-144 may be constituted as one printed circuit board comprising electronic circuitry such that for each electronic circuit one modular electronic part is provided.

The electronic circuits 141-144 (see FIG. 2) are each connected to one interface 101-104 for connecting a medical device 2 to the rack 1A, 1B, 1C. The interface serves as a mechanical as well as electrical connection for the medical device 2 and connects the medical device 2 to a power supply 11 as well as to a communication bus 12. The communication bus 12 connects all interfaces 101-104 with connections 105, 106, which can be connected either to another rack 1A, 1B, 1C or the network 7 (and via the network 7 to a control device 8). The connections 105, 106 and a further connection 107 are further connected to a power bus 13 and via the power bus 13 to the power supply 11. Via the connections 105-107, hence, a connection of the rack 1A, 1B, 1C to an external power supply as well as to other racks 1A, 1B, 1C for a power interconnection can be achieved.

The interfaces 101-104 as well as the connections 105-107 are arranged on a housing 10 of the rack 1A, 1B, 1C, which encompasses the power supply 11 and the internal identification means 14 comprising the electronic circuits 141-144.

Using the electronic circuit 141-144 the interface 101-104 associated with the particular electronic circuit 141-144 is identified. Since four interfaces 101-104 are present, two bits are sufficient to identify the (relative) position of the interfaces 101-104 on the rack 1A, 1B, 1C. For example, the lowest interface 104 may have the bit word 00, the interface 103 above the bit word 01, the next interface 102 the bit word 10 and the upper most interface 101 the bit word 11. Such bit words are hard-wired in the electronic circuits 141-144 and are provided to a medical device 2 attached to a particular interface 101-104. For example, if a medical device 2 is connected to the upper most interface 101, it receives from the associated electronic circuit 101 the bit word 11 and may communicate this information to the control device 8, which hence receives knowledge about the interface 101 the medical device 2 is attached to on the rack 1A, 1B, 1C.

Because further racks 1A, 1B, 1C may be present (see FIGS. 1 and 3), the identification of the interface 101-104 the medical device 2 is attached to on a particular rack 1A, 1B, 1C is not sufficient to identify the relative position of the medical device 2 in the entire vertical stack of medical devices 2 on the multiple racks 1A, 1B, 1C. For this reason, on the housing 10 of the rack 1A, 1B, 1C an input port 108 in combination with an output port 110 on a bottom side of the housing 10 and an input port 109 in combination with an output port 111 at a top side of the housing 10 are arranged. Such input ports 108, 109 and output ports 110, 111 serve to provide information about whether a further rack 1A, 1B, 1C is arranged above and/or below the rack 1A, 1B, 1C in question. If another rack 1A, 1B, 1C is arranged below the rack 1A, 1B, 1C, the further rack 1A, 1B, 1C is connected with the input port 108. If a further rack 1A, 1B, 1C is arranged above the rack 1A, 1B, 1C, the further rack 1A, 1B, 1C is connected to the input port 109.

The input port 108 is connected with all electronic circuits 141-144 via a line 145, and similarly the input port 109 is connected to all electronic circuits 141-144 by a line 146.

In the arrangement of FIG. 3, three racks 1A, 1B, 1C are arranged one above the other to form a vertical stack. Each rack 1A, 1B, 1C comprises two input ports 108, 109 and two output ports 110, 111, wherein the racks 1A, 1B, 1C are interconnected via the input ports 108, 109 and output ports 110, 111. In particular, the lowest rack 1C is connected via its input port 109 and its output port 111 to the input port 110 and the output port 108, respectively, of the rack 1B above. The rack 1B likewise is connected via its input port 109 and its output port 111 to the output port 110 and the input port 108, respectively, of the rack 1A above.

Via the input ports 108, 109 each rack 1A, 1B, 1C receives information whether a further rack 1A, 1B, 1C is arranged below or above the rack 1A, 1B, 1C in question. Likewise, via the output ports 110, 111 each rack 1A, 1B, 1C provides information about whether it is placed above or below another rack 1A, 1B, 1C.

On the basis of the information received via the input ports 108, 109, within the channel identification device 14 comprising the electronic circuits 141-144 an identification code is formed for each interface 101-104 such that each interface 101-104 of a rack 1A, 1B, 1C of the vertical stack of racks 1A, 1B, 1C assumes a unique identification code identifying it relative to the other interfaces 101-104 of the arrangement of racks 1A, 1B, 1C.

The identification code preferably is formed by a sequence of bits comprising several portions, wherein a first portion comprising two bits "AA" identifies the interface 101-104 on the particular rack 1A, 1B, 1C, a second portion representing one bit "C" may be set in dependence on whether a further rack 1A, 1B, 1C is arranged below the rack 1A, 1B, 1C in question, and a third portion representing one bit "B" may be set in dependence on whether a further rack 1A, 1B, 1C is arranged above the rack in question 1A, 1B, 1C.

The identification code hence becomes a sequence of bits having the shape of for example

CBAA.

If a rack 1A, 1B, 1C is arranged below the rack 1A, 1B, 1C in question, the corresponding bit "C" is set to 1, otherwise to 0. If a further rack 1A, 1B, 1C is arranged above the rack 1A, 1B, 1C in question, the corresponding bit "B" is set to 0, otherwise to 1.

Hence, in the example of FIG. 3, bit "B" for the lowest rack 1C assumes the value 0, and bit "C" assumes the value 0. For the rack 1B in the middle, bit "B" assumes the value 0, whereas bit "C" assumes the value 1. And for the uppermost rack 1A bit "B" assumes the value 1, and the bit "C" assumes the value 1.

Hence, in the example of FIG. 3, the medical device 2, for example an infusion pump, connected to the interface 103 of the lowest rack 1C obtains from the electronic circuit 143 associated with the interface 103 the identification code having the sequence of bits 0001, i.e. no rack is placed below and a rack 1B is placed above the rack 1C in question and the second interface 103 from the bottom is associated with the bits 01 hard-wired on the associated electronic circuit 143 of the rack 1C in question.

The medical device 2 connected to the interface 103 of the middle rack 1B obtains the identification code having the sequence of bits 1001, because a rack 1C is placed below and a rack 1A is placed above the rack 1B in question and the second interface 103 from the bottom is associated with the bits 01 hard-wired on the associated electronic circuit 143 of the rack 1B in question.

The medical device 2 connected to the interface 104 of the uppermost rack 1A obtains the identification code having the sequence of bits 1100, because a rack 1B is placed below, but no rack is placed above rack 1A in question and the interface 104 is associated with the bits 00 hard-wired on the associated electronic circuit 144 of the rack 1A in question. The medical device 2 connected to the interface 101 obtains the identification code having the sequence of bits 1111, because a rack 1B is placed below and no rack is placed above the rack 1A in question and the interface 101 is associated with the bit word 11 hard-wired on the associated electronic circuit 141 of the rack 1A in question.

Altogether, the interfaces 101-104 of the uppermost rack 1A are associated with identification codes ranging from 1100 to 1111, corresponding to the numeric numbers 12 to 15. The interfaces 101-104 of the middle rack 1B are associated with identification codes ranging from 1000 to 1011, corresponding to the numeric numbers 4 to 7, and the interfaces 101-104 of the lowermost rack 1C are associated with the identification codes of the sequences of bit 0000 to 0011 corresponding to the numeric numbers 0 to 3.

If only one rack is present the identification codes of the interfaces 101-104 of such rack range from 0100 to 0111, corresponding to the numeric numbers 8 to 11.

If two racks are present, the interfaces 101-104 of the upper rack are associated with the identification codes 1100 to 1111 corresponding to the numeric numbers 12 to 15. The lower rack is associated with the identification codes 0000 to 0011 corresponding to the numeric numbers 0 to 3.

Hence, if the number of racks 1A, 1B, 1C changes, also the identification codes of the interfaces 101-104 of each rack 1A, 1B, 1C change. In each case, however, each interface 101-104 of each rack 1A, 1B, 1C has a unique identification code which is transmitted to the medical device 2 attached to a particular interface 101-104 of a particular rack 1A, 1B, 1C and can be communicated from the medical device 2 to a control device 8, which hence receives information about the relative position of the medical device 2 on the racks 1A, 1B, 1C. With such information the control device 8 can display the medical device 2 in a position and order relative to other medical devices 2 connected to the racks 1a, 1B, 1C which matches the physical arrangement of the medical devices 2 on the racks 1A, 1B, 1C on the bedside of a patient.

With the described embodiment, the maximum number of racks 1A, 1B, 1C is limited to three, because the bit portions "CB" allow for a distinguishing of at most three racks 1A, 1B, 1C. A unique identification would not be possible anymore, if for example four racks 1A, 1B, 1C would be present, because the two middle racks 1A, 1B, 1C in that case would have the same bit portion "CB".

However, in principle the invention is also applicable to an arrangement of racks 1A, 1B, 1C having more than three racks 1A, 1B, 1C. In that case, via the inputs 108, 109 and the outputs 110, 111 it for example could be communicated between the racks 1A, 1B, 1C how many racks 1A, 1B, 1C are placed below a rack 1A, 1B, 1C and/or above the rack 1A, 1B, 1C, such that via such information again a unique identification code can be assigned to each interface 101-104 of each rack 1A, 1B, 1C.

The described solution for a maximum of three racks 1A, 1B, 1C has the advantage that it can be implemented in a very easy, inexpensive manner, because in principle it only needs to be detected whether a further rack 1A, 1B, 1C is connected above or below a rack 1A, 1B, 1C in question. This can be implemented in a very easy manner by using a simple detection circuitry, whereas a solution allowing for a connection of more than three racks 1A, 1B, 1C would require further communication circuitry.

The idea underlying the invention is not limited to the embodiments described above. In particular, also other medical devices 2 than infusion pumps can be connected to the racks. In principle, the racks do not need to form a vertical stack but could also be arranged side by side or in a matrix-like arrangement.

LIST OF REFERENCE NUMERALS 1A, 1B, 1C Rack
10 Housing
101-104 Interface for medical device
105-107 Connection
108, 109 Input port
110, 111 Output port
11 Power Supply
12 Communication bus
13 Power bus
14 Channel identification device
141-144 Electronic circuit
145, 146 Line
2 Medical device
3 Liquid container
30, 31 Infusion line
4 Patient's bed
5 Stand
6 Connection line
7 Network
8 Control device
80 Display device

The invention claimed is:

1. A method for arranging at least one medical device on a first rack, the method comprising:
attaching at least one medical device to at least one of a plurality of interfaces of the first rack to mechanically and electrically connect the at least one medical device to the first rack,
assigning, by a channel identification device of the first rack, comprising at least one electronic circuit, an identification code to each of the plurality of interfaces, providing, for a medical device connected with one of the plurality of interfaces, the identification code associated with the interface to the medical device or a control device connected to the medical device, and connecting at least one of a second rack to a first input port located at a first side of the first rack and a third rack to a second input port located at a second side of the first rack, wherein the at least one of the first input port and the second input port are connected to the channel identification device, wherein said step of assigning includes detecting, by the channel identification device, whether at least one of a second rack and a third rack are arranged on the first rack, and setting, by the channel identification device, the identification code based on the detection, wherein the identification code is a sequence of bits comprising a first portion indicating a sequential position of the interface the identification code is associated with on the first rack and at least one of a second portion indicating whether a second rack is arranged at a first side of the first rack, and a third portion indicating whether a third rack is arranged at a second side of the first rack, wherein said step of assigning includes setting, by the channel identification device, the at least one of the second portion and the third portion based on said detection whether at least one of a second rack and a third rack are arranged on the first rack.

2. The method according to claim 1, including the steps of:
receiving, by the at least one medical device, the identification code from the channel identification device and transmitting the identification code to a display device, and displaying, on the display device, the medical device with its topological position relative to other medical devices connected to the rack, or
transmitting, by the channel identification device, the identification code to the display device, and displaying, on the display device, the medical device with its topological position relative to other medical devices connected to the rack.

3. A system of racks for holding a plurality of medical devices, the system comprising:
a first rack comprising:
a plurality of interfaces for mechanically and electrically connecting at least one medical device to the first rack, and
a channel identification device comprising at least one electronic circuit configured to assign an identification code to each of the plurality of interfaces, wherein the channel identification device is operable to provide, for a medical device connected with one of the plurality of interfaces, the identification code associated with the interface to the medical device or a control device connected to the medical device,
wherein the first rack comprises at least one of a first input port to be connected to a second rack of the system located at a first side of the first rack and a second input port to be connected to a third rack of the system located at a second side of the first rack, wherein the at least one of the first input port and the second input port are connected to the channel identification device, the channel identification device being configured to detect whether at least one of a second rack and a third rack are arranged on the first rack, the channel identification device further being configured to set the identification code based on the detection, wherein the identification code is a sequence of bits comprising a first portion indicating a sequential position of the interface the identification code is associated with on the first rack and at least one of a second portion indicating whether a second rack is arranged at a first side of the first rack, and a third portion indicating whether a third rack is arranged at a second side of the first rack, wherein the channel identification device is configured to set the at least one of the second portion and the third portion based on said detection whether at least one of a second rack and a third rack are arranged on the first rack.

4. The system according to claim 3, wherein the number of interfaces of the first rack is four.

5. The system according to claim 4, wherein the channel identification device comprises a plurality of electronic circuits, wherein an electronic circuit is in operative connection with each of the plurality of interfaces and serves to assign the identification code to the associated interface.

6. The rack according to claim 4, wherein the channel identification device comprises a plurality of electronic circuits, wherein an electronic circuit is in operative connection with each of the plurality of interfaces and serves to assign the identification code to the associated interface.

7. The system according to claim 3, wherein the channel identification device comprises a plurality of electronic circuits, wherein an electronic circuit is in operative connection with each of the plurality of interfaces and serves to assign the identification code to the associated interface.

8. A system of racks for holding a plurality of medical devices, the system comprising:
a first rack, a second rack and a third rack, each of the first rack, the second rack and the third rack comprising a plurality of interfaces for mechanically and electrically connecting at least one medical device, and a channel identification device comprising at least one electronic circuit configured to assign an identification code to each of the plurality of interfaces, wherein the channel identification device is operable to provide, for a medical device connected with one of the plurality of interfaces, the identification code associated with the interface to the medical device or a control device connected to the medical device,
wherein the first rack comprises a first input port to be connected to the second rack located at a first side of the first rack and a second input port to be connected to the third rack located at a second side of the first rack, wherein the first input port and the second input port are connected to the channel identification device, the channel identification device being configured to detect whether at least one of the second rack and the third rack are arranged on the first rack, the channel identification device further being configured to set the identification code based on the detection, wherein the identification code is a sequence of bits comprising a first portion indicating a sequential position of the interface the identification code is associated with on the first rack, a second portion indicating whether a second rack is arranged at a first side of the first rack, and a third portion indicating whether a third rack is arranged at a second side of the first rack, wherein the channel identification device is configured to set the second portion and the third portion based on said detection whether at least one of a second rack and a third rack are arranged on the first rack.

9. The system according to claim 8, wherein the maximum number of racks of the system is three.

10. The system of claim 9, comprising at least one medical device connected to one of the multiple racks.

11. The system of claim 8, comprising at least one medical device connected to one of the first rack, the second rack and third rack.

12. The system according to claim 11, wherein the system comprises a display device which is in communication connection with at least one of the at least one medical device, the first rack, the second rack and the third racks and is configured to display the topological position of the at least one medical device relative to other medical devices connected to the first rack, the second rack and the third racks.

* * * * *